United States Patent [19]

Stookey

[11] E Re. 30,983

[45] Reissued Jun. 29, 1982

[54] COLORIMETRIC DETERMINATION OF IRON

[75] Inventor: Lawrence L. Stookey, Ames, Iowa

[73] Assignee: Hach Chemical Company, Ames, Iowa

[21] Appl. No.: 85,500

[22] Filed: Oct. 17, 1979

Related U.S. Patent Documents

Reissue of:

[64] Patent No.: 3,836,331
Issued: Sep. 17, 1974
Appl. No.: 352,734
Filed: Apr. 19, 1973

U.S. Applications:

[62] Division of Ser. No. 49,579, Jun. 24, 1970.

[51] Int. Cl.[3] ..... G01N 31/22; G01N 33/18; G01N 33/20

[52] U.S. Cl. ..... 23/230 R; 23/230 B; 252/408

[58] Field of Search ..... 23/230 R, 230 B; 252/408

[56] References Cited

U.S. PATENT DOCUMENTS

| | | | |
|---|---|---|---|
| 2,963,349 | 12/1960 | Bernard et al. | 23/230 |
| 3,095,382 | 6/1963 | Hach | 252/408 |
| 3,506,403 | 4/1970 | Fryer et al. | 23/230 |
| 3,537,822 | 11/1970 | O'Malley et al. | 23/230 |
| 3,667,915 | 6/1972 | Klein | 23/230 B |

OTHER PUBLICATIONS

Ferrozine-A New Spectrophotometric Reagent for Iron, Stookey, Anal. Chem., vol. 42, No. 7, 6/70, p. 779.

P. Trinder, "The Improved Det. of Iron in Serum," J. Clin. Pathol. 9:170 (1956).

J. W. Landers et al., Am. J. Clin. Pathol. 29:590 (1958), Det. of Serum Copper and Iron in a Single Small Sample.

B. Zak, "Simple Proc. for the Single Sample Det. of Serum Copper and Iron", 3:328 (1958), Clin. Chim. Acta.

D. Blair et al., Bathophenanthroline Disulfonic Acid & Bathocuproinesulfonic Acid, Water Soluble Reagents for Iron & Copper, Talanta 7:163 (1961).

Cryberg et al., Sulfonation of Bathophenanthroline & Bathocuproine, Proc. Iowa Acad. of Sci., 70:184 (1963).

C. R. Noller, Chem. of Organic Compounds, (2nd Ed. 1957), p. 466.

Ogata et al., Chem. Abstracts 63:5648 (1965).

Case, Prep. of Hydrazines & as-Triazines Related to Substituted 2 Cyanopyridines, J. Org. Chem. 39-931, (1965).

Schilt, "Some New Chromogens for Iron, Cobalt and Copper", Talanta 13:895, (1966).

B. Zak, 2,6-Bis(4 Phenyl-2-pyridyl)-4 phenyl-pyridine as an Aqueous Micro-Iron Reagent Microchem. J., 3/69, vol. 14, p. 155.

C. R. Gibbs, Characterization & Application of Ferro-Zine Iron Reagent as a Ferrous Iron Reagent, Anal. Chem. 48:1197 (1976).

A. Manasterski et al., "Spectrophotometric Study of the Reaction of 3-(2-Pyridyl)-5,6-bis (4-phenylsulfonic acid)-1,2,4-triazine with Iron & Copper", Micro Chem. J., 16:245, (1971).

H. Diehl et al., "The Iron Reagents . . . ", G. F. Smith Chem. Co., 1965.

P. Carter, Spect. Det. of Serum Iron at the Submicrogram Level with a New Reagent (Ferrozine), Anal. Biochem. 40:450, (1971).

Schilt et al., Imp. Sens. & Selectivity in the Spectro. Det. of Iron by use of a New Ferrain Type Reagent, Analy. Chem., 39:115, (1967).

D. E. Blair et al., "Sulfonic Acid Derivatives of 1,10--Phenanthroline," *Analytical Chemistry,* vol. 33, p. 867, (1961).

A. A. Schilt, *Analytical Applications of 1,10-Phenanthroline and Related Compounds,* p. 55 (1969).

*Primary Examiner*—Michael S. Marcus

*Attorney, Agent, or Firm*—Leydig, Voit, Osann, Mayer & Holt, Ltd.

[57] ABSTRACT

3-(2-pyridyl)-5,6-bis(phenylsulfonic acid)-1,2,4-triazine and certain salts thereof, e.g. sodium, are provided together with a method for forming such compounds. These compounds are useful as reagents in the spectrophotometric determination of iron in water or other solutions.

2 Claims, No Drawings

COLORIMETRIC DETERMINATION OF IRON

Matter enclosed in heavy brackets [ ] appears in the original patent but forms no part of this reissue specification; matter printed in italics indicates the additions made by reissue.

This is a division of application Ser. No. 49,579, filed June 24, 1970.

This relates to novel chemical compounds and, more particularly, to compounds which may be advantageously employed in chemical analyses for iron.

There are a wide variety of applications wherein it is desirable to determine the presence of iron in water or other solutions. For example, it is necessary to analyze for the iron content in the boiler water in a steam electric power-generating plant because the iron oxide content of the water is an index of the rate of corrosion taking place in the boiler.

In carrying out the conventional methods for analysis of iron, the first step involves solubilizing the solid iron compounds in the test sample. This is typically achieved by adding an acid such as hydrochloric acid to the sample and then allowing sufficient time for the solid iron compounds to dissolve. Because dissolution proceeds slowly at room temperatures, the sample is generally heated to boiling for the time necessary to achieve solubilizing. A reagent such as hydroxylammonium chloride is then added to reduce the iron to the ferrous form. This latter reagent is sometimes combined with the hydrochloric acid addition to minimize the number of steps involved.

A reagent is then added to the test sample solution (suitably buffered to a pH value determined by the reagent being used as is well known) which will form a colored complex with the iron at the pH level involved. The iron content is then determined colorimetrically by well known means. Commercial analyzers capable of continuously carrying out the hereinbefore described method are available.

Compounds termed "ferroin" reagents have been widely used as the colorimetric reagent for the iron analysis hereinbefore described. These organic molecules, containing the atomic configuration.

$$-N{=}\overset{|}{C}-\overset{|}{C}{=}N-,$$

react as bidentate ligands with certain metal ions including ferrous ions to give colored complexes. This effect was first noticed with the ferrous ion; and, since the ferrous complexes are generally of a more intense color than with other metals, the atomic configuration was given the trivial name of the "ferroin" group.

While hundreds of compounds containing the ferroin group have been synthesized and the majority of these demonstrate the ability to form complexes with the ferrous ion, most of these are either only weakly colored, or are unstable under normal physical conditions or are formed only over a very narrow pH range.

A few of these compounds, however, form stable, highly colored species with the ferrous ion and are therefore suitable for use as colorimetric reagents for the quantitative determination of iron. Examples of compounds that have found acceptance are 1,10-phenanthroline; 4,7-diphenyl-1, 10-phenanthroline; 2,2'-bipyridyl; 2,6-bis(2-pyridyl)pyridine; 2,4,6-tris (2-pyridyl)-1,3,5-triazine; and phenyl 2-pyridyl ketoxime.

Most of these reagents are the products of difficult and tedious organic syntheses together with the fact that the raw materials are relatively expensive. Accordingly, while the cost of a manual classical laboratory analysis is fairly small due to the small quantity of reagent involved, the cost of employing such expensive ingredients in operating an automatic continuous analyzer would be prohibitive.

Recently, Case reported the preparation of 24 new compounds (30 J. Org. Chem., 931, 1965) which may have some application as chromogens for iron, cobalt and copper. These were later tested by Schilt (13 Tatanta, 895–902, 1966).

Among these compounds was a substituted triazine, i.e. 3-(2-pyridyl)-5,6-diphenyl-1,2,4-triazine. While this material is a good reagent for the determination of iron, it, like other high molecular weight compounds containing the ferroin group, suffers the disadvantage of being quite insoluble in water as is the complex which it forms with the ferrous ion.

While this insolubility does not present any problems in carrying out a laboratory analysis for the determination of iron, the insolubility eliminates, from a practical standpoint, the compound as a reagent for use as a reagent in a completely automated analysis.

It is accordingly an object of the present invention to provide a sensitive spectrophotometric reagent for iron which may be advantageously employed in completely automated analysis techniques. A related and more specific object provides novel ferroin compounds which are water soluble.

A further object lies in the provision of an economical method for forming a spectrophotometric reagent for iron.

A still further object provides a spectrophotometric reagent of the above-identified type which is stable, both in air and in an aqueous solution.

Another object is to provide a reagent of the above-identified type which may carry out the determination with only a minimum of interferences.

Other objects and advantages of the present invention will become apparent as the following description proceeds.

While the invention is susceptible of various modifications and alternative forms, certain specific embodiments thereof have been shown by way of examples which will be described in detail herein. It should be understood, however, that it is not intended to limit the invention to the particular forms disclosed, but, on the contrary, the intention is to cover all modifications, equivalents and alternatives falling within the spirit and scope of the invention.

Briefly, the present invention provides a spectrophotometric reagent comprising 3-(2-pyridyl)-5,6-bis(phenylsulfonic acid)-1,2,4-triazine or certain soluble salts thereof such as the disodium, the diammonium or the dipotassium salt, the corresponding mono salts, or mixtures thereof. The principal product has the sulfuric acid groups at the 4-position and these have the following structural formula:

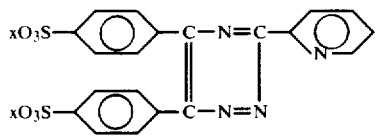

wherein x is a member selected from the group consisting of hydrogen, sodium, potassium or ammonium. The sensitivity of the subject reagent, measured as the molar extinction coefficient at the wavelength of maximum absorbance (i.e. 562 nm.) is greater than the previously described compound prepared by Case as well as other prior ferroin reagents. Thus, its sensitivity is 27,800 (moles$^{-1}$ cm$^{-1}$) as compared with values of 11,100 for 1,10-phenanthroline, 22,143 for 4,7-diphenyl-1, 10-phenanthroline, and 22,600 for 2,4,6-tris(2-pyridyl) 1,3,5-triazine.

In addition, the ferrous complex is stable over a wide pH range, i.e. from about 4 to about 9; and, once the complex is formed in this range, the solution may be made 1 N with respect to perchloric, nitric, or hydrochloric acids without any noticeable fading taking place for several hours.

The reagent itself is stable in air and in aqueous solution and is not susceptible to chemical destruction except under the most drastic conditions. Positive interferences are limited to cuprous and cobaltous ions, both of which form slightly yellow complexes and do not substantially interfere until they are present in large excess over the ferrous ion. Negative interferences occur only with cyanide and hydrosulfite in large concentration.

To prepare the subject reagent in accordance with the present invention, 2-pyridyl hydrazidine, a first intermediate, is formed. This is achieved by providing a reaction mixture of hydrazine (preferably anhydrous) and 2-cyanopyridine (both relatively inexpensive commercially available compounds) in a solvent such as isopropanol (again preferably anhydrous). The reaction mixture is stirred at room temperature for about 4 hours. The proportions are not critical; however, it is preferred to employ an excess of hydrazine (up to about 100 percent or more) so that the reaction will go to substantial completion. The reaction mixture is then cooled to from about 0° to 10° C. with the intermediate, 2-pyridyl hydrazidine, crystallizing out as a white precipitate.

The hydrazidine intermediate is then treated to remove any hydrazine impurities. This may be typically achieved by washing with a solvent, suitably ice cold isopropanol. Removal of the impurity is believed to prevent discoloration of the subsequent intermediate which might otherwise occur.

This intermediate is then dissolved in a solvent such as isopropanol and a stoichiometric amount of benzil is dissolved in a separate solvent, which may again be isopropanol. Using an excess of benzil is not preferred since it could conceivably contaminate the product and cause decomposition during subsequent steps, such as sulfonation. Both of these reactant solutions may be heated to 40° to 60° C. to increase the amount of reactant which may be placed in the given amount of solvent which is being employed. 3-(2-pyridyl)-5,6-diphenyl-1,2,4-triazine is then formed by adding the two reactant solutions to each other.

Typically, this is carried out by adding the hydrazidine to the benzil with stirring. The reaction is slightly exothermic and within a few minutes a white precipitate begins to form (a yellow precipitate may be formed if not all the hydrazine was removed or the temperature involved in preparing the hydrazidine was too high). After about 30 to 60 minutes with stirring, the formed precipitate is filtered and washed at room temperature with isopropanol to free the precipitate of any unreacted materials. This material is then dried at room temperature and passed through a suitable mesh screen to provide uniform sized particles (e.g. 20 mesh).

In accordance with the present invention, the reagent compounds of the present invention are then formed by sulfonating the ground material. This is typically carried out by adding at least a stoichiometric amount of fuming sulfuric acid to the ground material at room temperature with stirring. The reaction is exothermic and will raise the reaction temperature to about 120° C. and the partially sulfonated product will go into solution quite rapidly.

At this point, and in accordance with another aspect of the present invention, additional heat is provided to bring the temperature of the reaction mixture up to about 200° C. (±5° C.) in as little time as possible. If the temperature of the reaction mixture is not brought within this range, complete sulfonation will not result. Additionally, if the temperature is not brought rapidly to this temperature, the prolonged contact at elevated temperatures with the fuming sulfuric acid will result in degradation of the organic intermediate. The timing involved in raising the temperature to about 200° C. may be up to about 30 minutes or so; however, it is preferred to bring the temperature up to this point within about 15 to 20 minutes or even less.

This reaction is not time dependent; and, after the reaction temperature has been advanced to 200° C. or thereabouts, the external heat is removed and the reaction mixture is cooled to about 30° to 50° C. as quickly as possible. The existence of the disulfonic acid may be confirmed by organic microanalysis. Infared evidence suggests that the sulfonic acid groups occupy the 4-position and this is the majority of the product. It should be appreciated that minor portions of the product may have the sulfonic acid groups at other positions.

When it is desired to form a salt, the resulting soluble product may then be added to a salt solution which is very nearly saturated. For example, when the solution is a sodium chloride brine, a light yellow precipitate will form over a period of time, which is predominantly the disodium salt. Minor impurities such as sodium chloride and sodium sulfate may be also formed but these do not interfere with the function of the disodium organic salt as a spectrophotometric reagent for iron. These impurities may, however, be easily removed by crystallizing from water.

Further processing typically involves drying the precipitate as a cake and then grinding up. For use as a reagent, the ground-up product may then be dissolved in a quantity of water to form an aqueous reagent.

The following example is merely exemplary as to how the present invention could be carried out. It is representative of this invention and should not be considered in limitation thereof.

EXAMPLE 2.0 liters of isopropanol, 600 grams of anhydrous hydrazine and 678 grams of 2-cyanopyridine are added to a 5-liter round-bottomed flask. The resulting reaction mixture is stirred for about 4 hours. The reaction mixture is then cooled until its temperature is below about 15° C. The cooled reaction mixture is then filtered through a medium filter paper and the white crystals of 2-pyridylhydrazidine are washed thoroughly with isopropanol at 0° C. to remove all possible hydrazine.

1370 grams of benzil are then dissolved in 15 liters of is opropanol, using a 22-liter flask with mantle and stirring. Heating to a temperature of from about 50° to 55° C. should be sufficient. All the 2-pyridylhydrazidine is dissolved in a minimum amount of isopropanol (about 5-liters), with heating only if necessary.

The solution of the 2-pyridylhydrazidine is then added to the solution of the benzil with stirring for about 1 hour. A precipitate should form within several minutes.

The reaction mixture is filtered through a medium filter paper. The resulting cake of 3-(2-pyridyl)-5,6-diphenyl-1,2,4-triazine is rinsed well with isopropanol and then air dried at room temperature.

The 3-(2-pyridyl) 5,6-diphenyl-1,2,4-triazine (about 2 kilograms) is placed in a 5-liter round-bottomed flask with a wide neck. 3 liters of fuming sulphuric acid is added to the flask. The solution is heated to about 200° C. with an open flame as quickly as possible. The heating is then ceased and a small fan directed against the flask which is stirred constantly so that the temperature drops several degrees per minute.

When the temperature has fallen below about 50° C., 14 liters of saturated sodium chloride solution in a 22-liter flask is prepared. While stirring the sodium chloride solution, the contents of the 5-liter flask are slowly added to the flask containing the sodium chloride solution via a separatory or additional funnel. The addition should take about 2 hours.

The resulting suspension is then filtered through medium paper, the cake dried and rinsed with methanol. The final product represents the sodium salts of 3-(2-pyridyl)-5,6-bis(phenylsulfonic acid)-1,2,4-triazine, the principal portion being the disodium salt.

Thus, as has been seen, a spectrophotometric reagent for ferrous iron has been provided by the present invention which is soluble in water, may be economically formed from readily available raw materials and which functions with a minimum of interferences. The reagent is amply suited to either manual analysis or continuous automatic instrumental analysis for on-stream monitoring. The sensitivity of the reagent exceeds that of any of the commercially available iron reagents.

I claim as my invention:

1. In a method for quantitatively determining the presence of iron in a sample solution which includes adding a reagent to a sample solution containing iron in the ferrous state to form a colored complex and colorimetrically determining the iron content, the improvement comprising using 3-(2-pyridyl)-5,6-bis(phenylsulfonic acid)-1,2,4 triazine as the reagent *to provide greater sensitivity as compared to that obtained with 3-(2-pyridyl)-5,6-diphenyl-1,2,4-triazine.*

2. The method of claim 1 wherein the sulfonic acid groups are located at the 4-position.

* * * * *